(12) United States Patent
Ross et al.

(10) Patent No.: US 6,183,488 B1
(45) Date of Patent: Feb. 6, 2001

(54) VACUUM RING WITH LINEAR BEARINGS FOR AN AUTOMATED CORNEAL SHAPER

(75) Inventors: Rod Ross, Laguna Niguel; Gregory Hughes, Fountain Valley, both of CA (US)

(73) Assignee: Med-Logics, Inc., Laguna Niguel, CA (US)

( * ) Notice: Under 35 U.S.C. 154(b), the term of this patent shall be extended for 0 days.

(21) Appl. No.: 09/186,995

(22) Filed: Nov. 6, 1998

(51) Int. Cl.[7] .................................................... A61F 9/00
(52) U.S. Cl. ............................................................... 606/166
(58) Field of Search ....................................... 606/166, 161

(56) References Cited

U.S. PATENT DOCUMENTS

| | | |
|---|---|---|
| Re. 35,421 * | 1/1997 | Ruiz et al. ............................. 606/166 |
| 2,480,737 | 8/1949 | Jayle . |
| 3,583,403 | 6/1971 | Pohl et al. . |
| 4,173,980 | 11/1979 | Curtin . |
| 4,205,682 | 6/1980 | Crock et al. . |
| 4,429,696 | 2/1984 | Hanna . |
| 4,660,556 | 4/1987 | Swinger et al. . |
| 4,662,370 * | 5/1987 | Hoffmann et al. ..................... 606/166 |
| 4,665,914 | 5/1987 | Tanne . |
| 4,674,503 | 6/1987 | Peyman et al. . |
| 4,688,570 | 8/1987 | Kramer et al. . |
| 4,807,623 | 2/1989 | Lieberman . |
| 4,884,570 | 12/1989 | Krumeich et al. . |
| 4,903,695 | 2/1990 | Warner et al. . |
| 4,997,437 * | 3/1991 | Grieshaber ............................ 606/166 |
| 5,133,726 * | 7/1992 | Ruiz et al. ............................. 606/166 |
| 5,215,104 | 6/1993 | Steinert . |

OTHER PUBLICATIONS

Bores Eye Institute, Lamellar Refractive Keratoplasty, 1988.*

Steinway Instrument Company, Inc., The Steinway/Barraquer In–Situ Microkeratome Set.

* cited by examiner

Primary Examiner—Michael Buiz
Assistant Examiner—(Jackie) Tan-Uyen T. Ho
(74) Attorney, Agent, or Firm—Irell & Manella LLP

(57) ABSTRACT

A medical device that can be used to cut a cornea. The device may include a head that houses a blade. The head and blade can be moved across a ring by a drive assembly. The drive assembly may also move the blade relative to the head to resect the cornea. The head may have a pair of tongues that can slide along corresponding grooves in the ring. The tongues and grooves may be configured so that the head can be loaded onto the ring from a vertical direction.

14 Claims, 7 Drawing Sheets

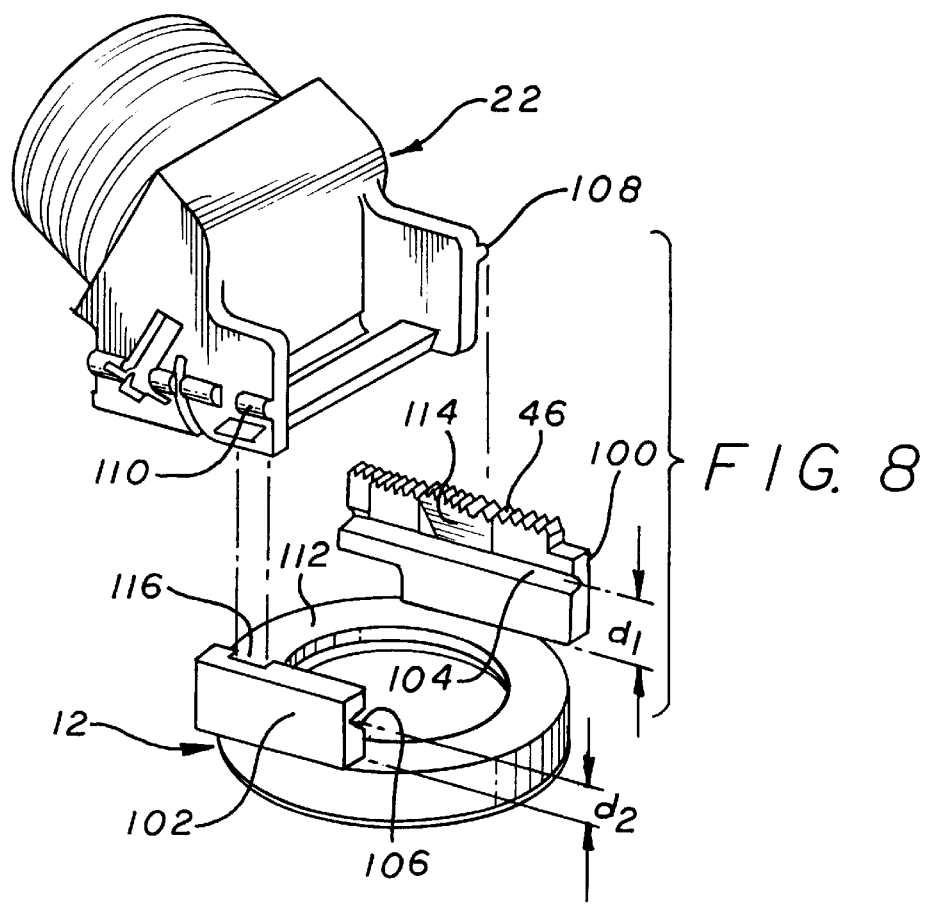
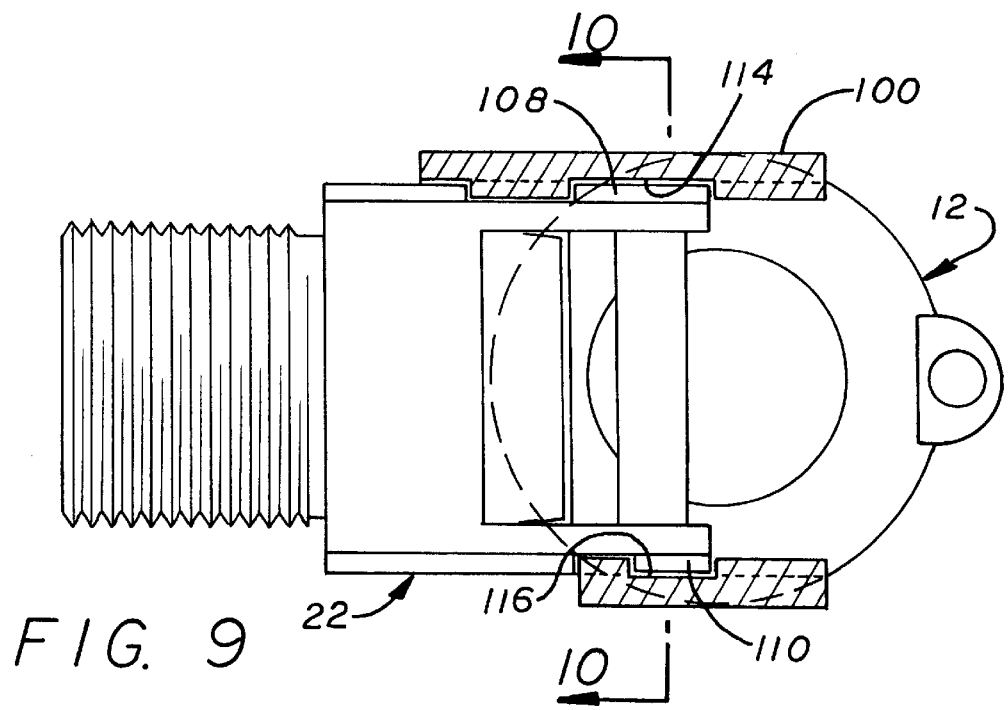

VACUUM RING WITH LINEAR BEARINGS FOR AN AUTOMATED CORNEAL SHAPER

BACKGROUND OF THE INVENTION

1. Field of the Invention

The present invention relates to a microkeratome that can be used to remove tissue from a cornea.

2. Background Information

There have been developed a number of different surgical techniques to correct hyperopic or myopic conditions of a human eye. U.S. Pat. No. 4,840,175 issued to Peyman discloses a procedure wherein a thin layer of corneal tissue is cut and removed from a cornea. A laser beam is then directed onto the exposed corneal tissue in a predetermined pattern. The laser beam ablates corneal tissue and changes the curvature of the eye.

U.S. Pat. No. Re. 35,421 issued to Ruiz et al. discloses a device for cutting the cornea to expose an underlying surface for laser ablation. Such a device is commonly referred to as a microkeratome. The Ruiz microkeratome includes a ring that is placed onto a cornea and a blade that is located within an opening of the ring. The device also contains a drive mechanism which moves the blade across the cornea in a first direction while sliding the blade across the eye in a second transverse direction. The device can create a lamella which is flipped back so that the eye can be ablated with the laser.

The Ruiz microkeratome includes a head that houses the blade. The drive mechanism of the keratome moves the head and the blade across the opening of the ring. The head and ring have a pair of dovetail tongue and groove linear bearings which insure that the blade moves in a linear manner across the cornea.

The dovetail configuration of the Ruiz microkeratome requires that the head be loaded from the side of the ring. The surgeon must align the dovetail features before sliding the head onto the ring. Aligning the dovetail features can be difficult and awkward. It would be desirable to provide a microkeratome that can be more readily assembled than keratomes of the prior art.

SUMMARY OF THE INVENTION

One embodiment of the present invention is a medical device that can be used to cut a cornea. The device may include a head that houses a blade. The head and blade can be moved across a ring by a drive assembly. The drive assembly may also move the blade relative to the head to resect the cornea. The head may have a pair of tongues that can slide along corresponding grooves in the ring. The tongues and grooves may be configured so that the head can be loaded onto the ring from a vertical direction.

BRIEF DESCRIPTION OF THE DRAWINGS

FIG. 8 is an exploded view of an alternate embodiment of a head and a ring;

FIG. 9 is a cross-sectional view of the head and ring;

DETAILED DESCRIPTION

Figure 1:
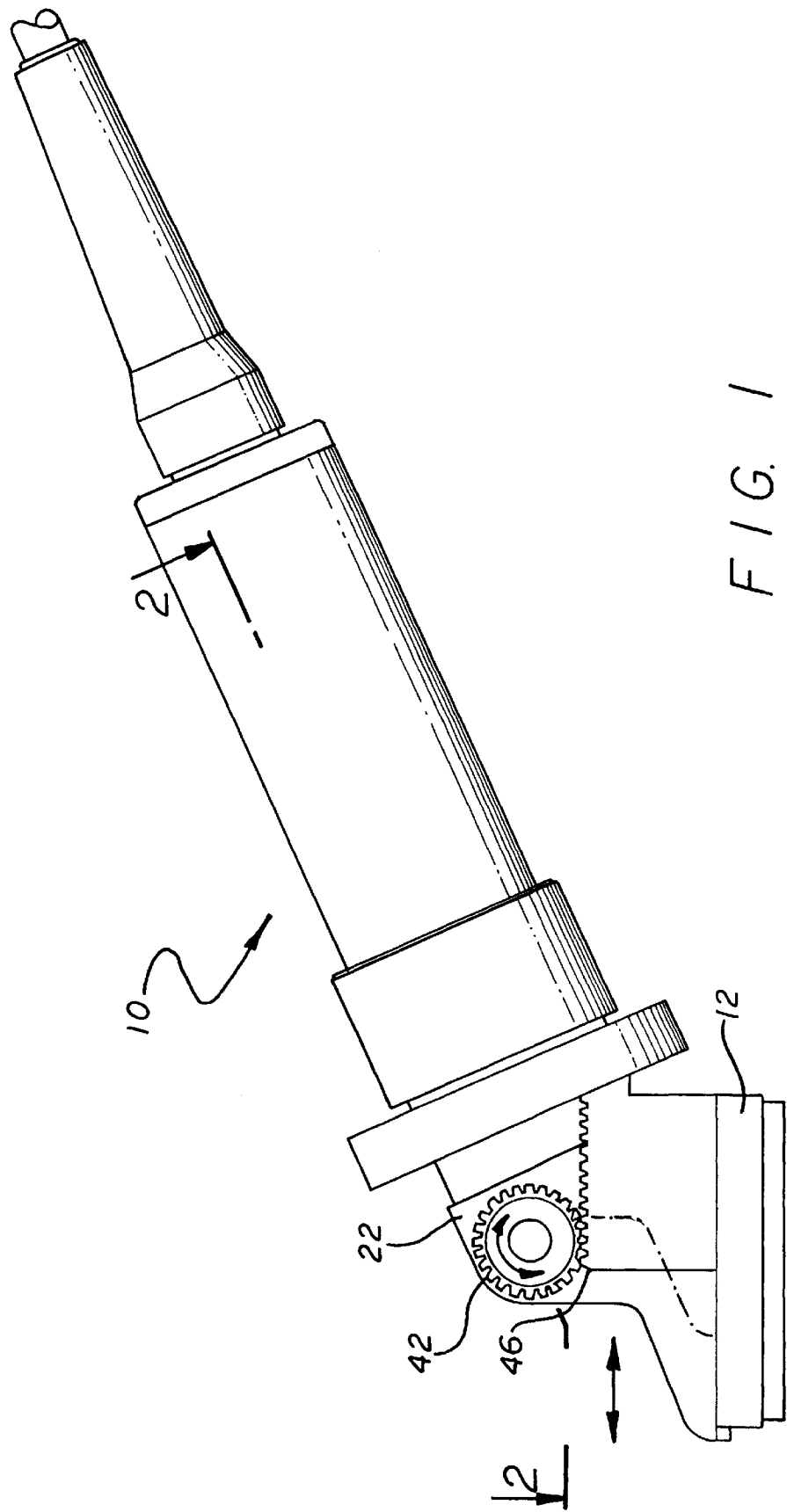
FIG. 1 is a side view of an embodiment of a medical device of the present invention.

Referring to the drawings more particularly by reference numbers, FIGS. 1–5 show an embodiment of a medical device 10 of the present invention. The device 10 may include a ring 12 that is placed onto a cornea (not shown). The ring 12 may have a port 14 which is coupled to a vacuum source (not shown). The vacuum source may create a vacuum pressure that pulls the ring 12 onto the cornea. The vacuum pressure prevents the ring 12 from moving during a procedure.

The device 10 may have a blade 16 that is located within an opening 18 of the ring 12. The blade 16 can move within the opening 18 in a first direction and a second transverse direction. The simultaneous movement of the blade 16 can create a cut across the surface of the eye. The device 10 may include a plate 19 that is mounted to the ring 12 and which flattens the cornea.

The blade 16 is attached to a blade holder 20. The blade holder 20 is attached to a head 22. The head 22 and blade holder 20 both move with the blade 16 relative to the ring 12. The blade holder 20 moves in the second direction while being pulled in the first direction. The head 22 only moves in the first direction.

Figure 2:
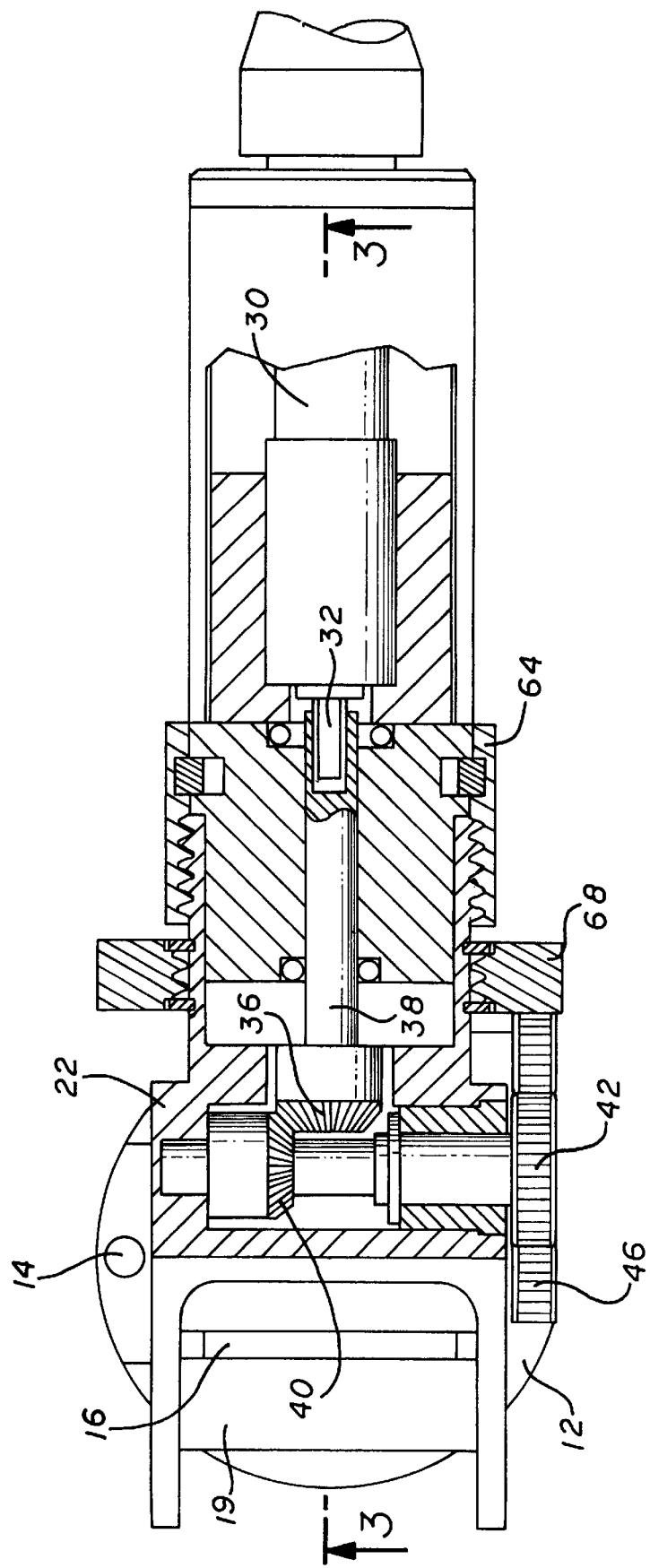
FIG. 2 is a cross-sectional view taken at line 2—2 of FIG. 1.
Figure 3:
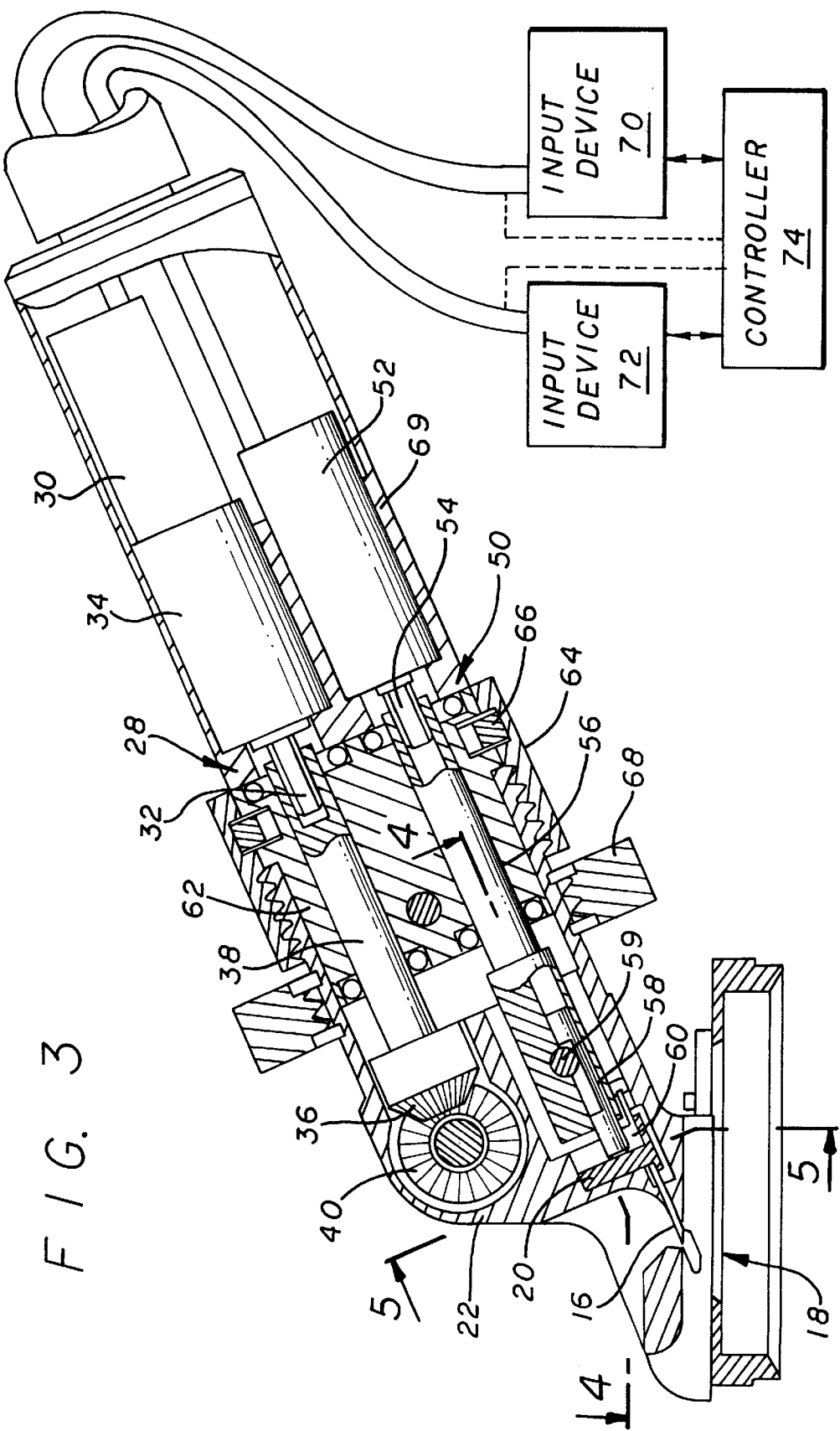
FIG. 3 is a cross-sectional view taken at line 3—3 of FIG. 2.

Referring to FIGS. 2 and 3, the device 10 includes a first drive mechanism 28 which moves the head 22, the blade holder 20 and the blade 16 in the first direction. The first drive mechanism 28 may include a first motor 30 that is coupled to an output shaft 32 by a gear reduction box 34. By way of example, the motor 30 may be an electric motor. The motor 30 may be coupled to a first gear 36 by a shaft 38 that is attached to the output shaft 32.

The first gear 36 may be coupled to a second gear 40 that is mounted to the head 22. The second gear 40 may be connected to a third gear 42 by a shaft 44. The third gear 42 may be coupled to a gear rack 46 (see also FIG. 1). The first 36 and second 40 gears may be of the bevel type so that rotation of the motor output shaft 32 imparts a corresponding rotation of shaft 44 and third gear 42. Rotation of the third gear 42 along the gear rack 46 causes the head 22, blade holder 20 and blade 16 to move in the first direction.

As shown in FIG. 1, the gear rack 46 may be located on a pedestal 48 that is attached to the ring 12. The pedestal 48 elevates the rack 46 above the cornea so that there is a low probability of an eye lash becoming stuck in the rack and pinion gear assembly.

Figure 4:
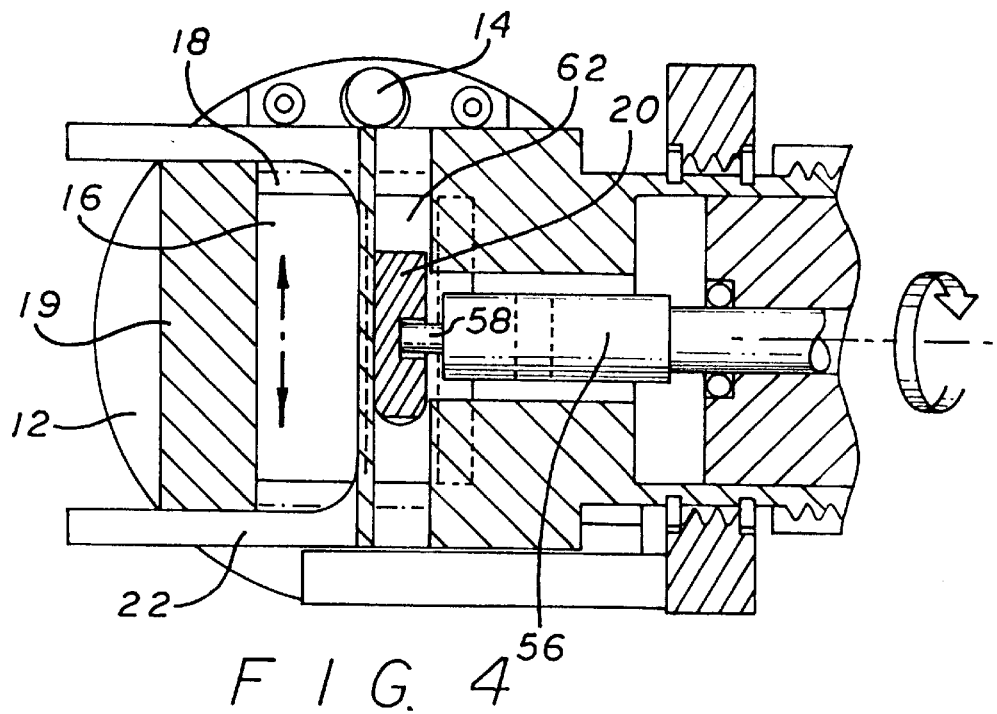
FIG. 4 is a cross-sectional view taken at line 4—4 of FIG. 3.
Figure 5:
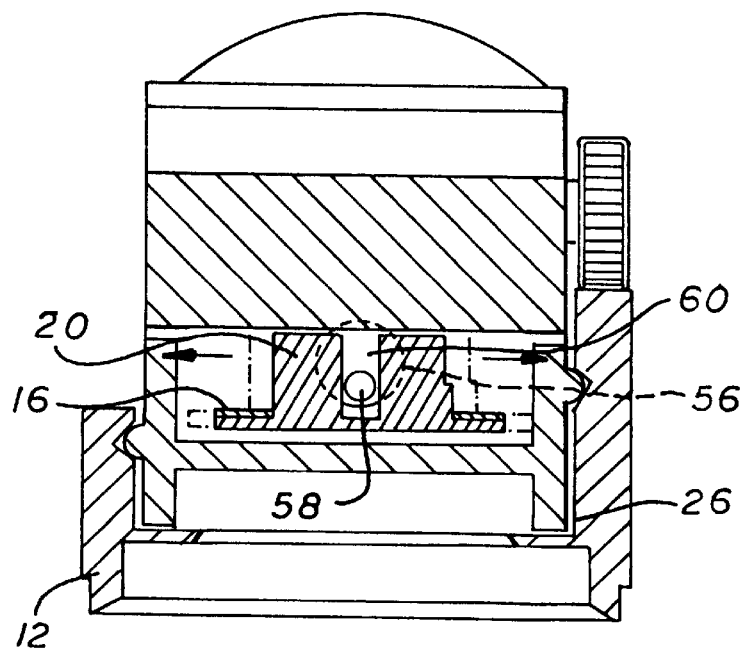
FIG. 5 is a cross-sectional view taken at line 5—5 of FIG. 3.

Referring to FIGS. 3–5, the device 10 may also have a second drive mechanism 50 that moves the blade holder 20 and the blade 16 in the second direction. The second drive mechanism 50 may include a second motor 52 which has an output shaft 54. By way of example, the motor 52 may be an electric motor. The output shaft 54 may be attached to a shaft 56 which has an eccentric cam pin 58. The cam pin 58 may be captured within the shaft 54 by another pin 59. The eccentric cam pin 58 fits within a slot 60 of the blade holder 20.

Rotation of the motor output shaft 54 moves the pin 58 about the center axis of the shaft 56. The eccentric rotation of the pin 58 moves the blade holder 20 and blade 22 within a slot 62 of the head 22 in the second direction. The pin 58 slides along the blade holder slot 60 in a vertical direction so that the blade 16 does not move into and out of the cornea.

The output shafts 38 and 56 may extend through a bulkhead 62 that is partially located within the head 22. A collar 64 and clip 66 attach the bulkhead 62 to the head 22. The device 10 may further have a lacking ring 68 for the collar 64. The motors 30 and 52 may be housed within a motor casing 69.

The first motor 30 may be connected to a first input device 70. The second motor 52 may be connected to a second input device 72. By way of example, the input devices 70 and 72 may be foot pedals which can be operated by a surgeon to control the actuation and speed of the motors 30 and 52. This allows the surgeon to separately control the movement of the blade 16 in the first direction and the movement of the blade 16 in the second direction. The surgeon can thus vary the shape and size of the cut.

The device 10 may further include a controller 74 which can be programmed to control the first 28 and second 50 drive mechanisms. The controller 74 can be used in conjunction with the input devices 70 and 72. The controller 74 may have programmable limit functions which limit the speed of the motors 30 and 52.

Figure 6:
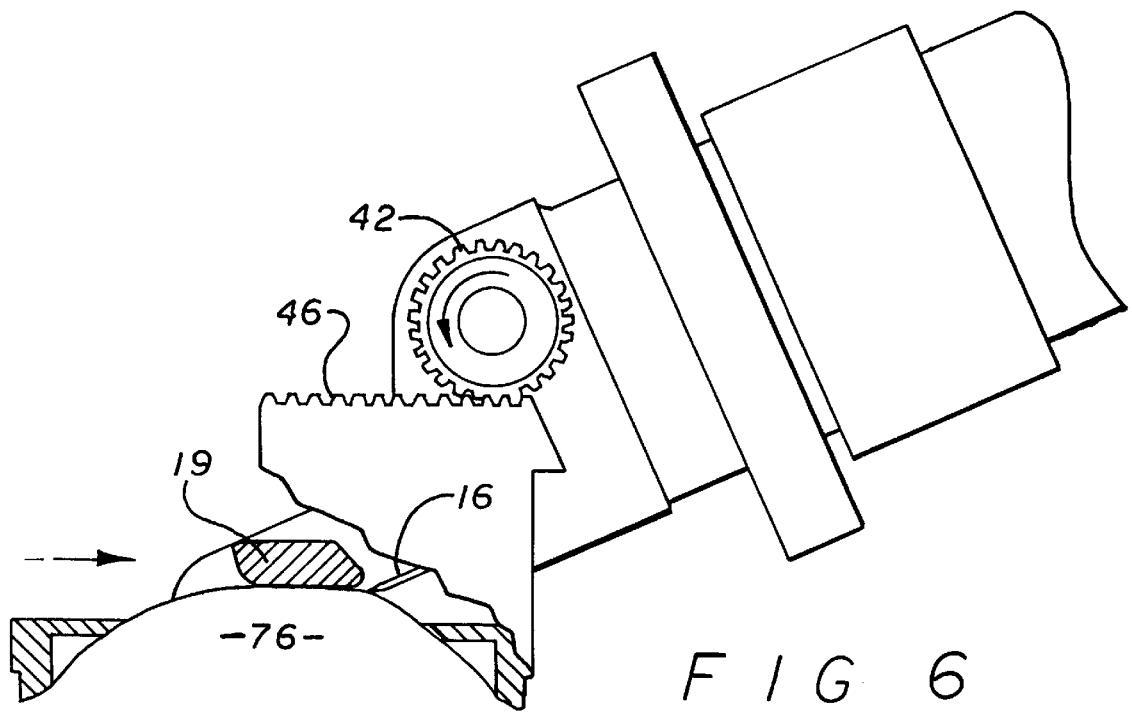
FIG. 6 is a side sectional view showing the device placed on a cornea.
Figure 7:
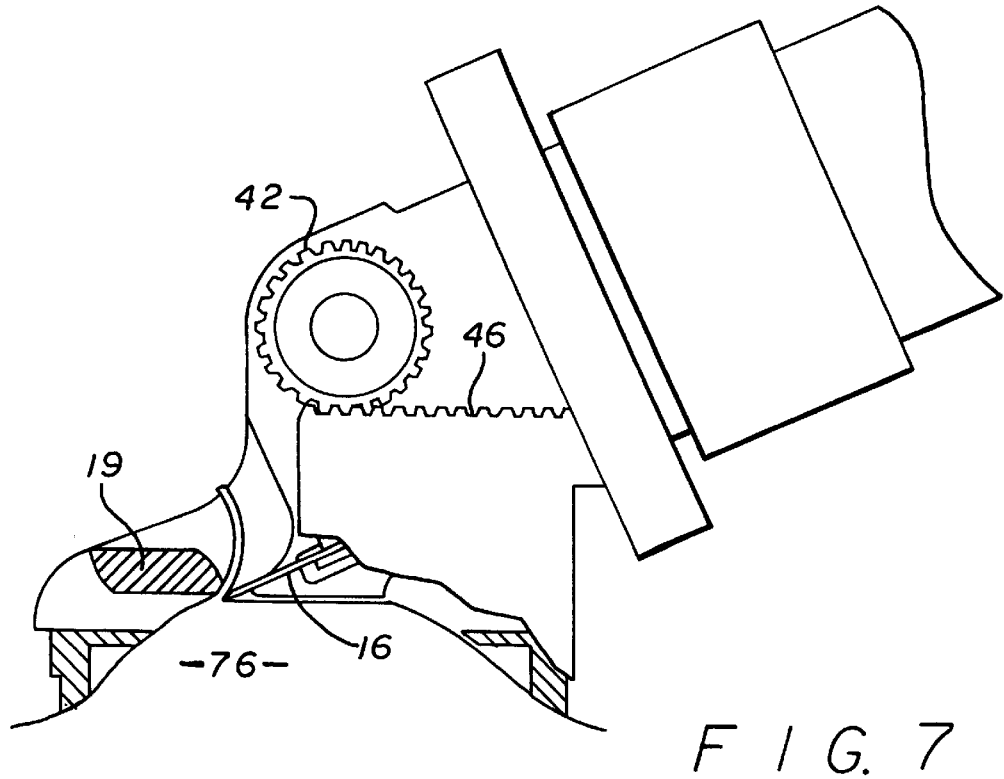
FIG. 7 is a side sectional view showing the device cutting the cornea.

As shown in FIGS. 6 and 7, in operation the ring 12 is placed on a cornea 76. The plate 19 tends to flatten the cornea 76 adjacent to the blade 16. The surgeon actuates the first 28 and second 50 drive mechanisms to move the blade 16 in the first and second directions. The movement of the blade cuts the cornea 76.

FIGS. 8 and 9 show linear bearings of the head 22 and the ring 12. The medical device 10 may utilize tongue and groove bearings to couple the head 22 to the ring 12. The tongue and groove linear bearings may be configured so that the head 22 can be inserted into the ring 12 from a vertical direction. This is to be distinguished from the dovetail arrangements used in the prior art where the head 22 must be inserted from a horizontal direction.

The ring 12 may have a first sidewall 100 and a second sidewall 102. The first sidewall 100 may include the gear rack 46 that is coupled to the third gear 42 shown in FIG. 1. Each sidewall 100 and 102 may have a generally V-shaped groove 104 and 106, respectively. The grooves 104 and 106 may extend along the entire length of each wall 100 and 102.

The head 22 may have a pair of tongues 108 and 110. Tongue 108 can be inserted into groove 104. Likewise, tongue 110 can be inserted into groove 106 so that the head 22 can slide across the ring 12. Each tongue 108 and 110 preferably has a radial outer surface. The radial surface of each tongue 108 and 110 creates contact at two points of each V-shaped groove 104 and 106. The two point contact aligns the tongues 108 and 110 within the grooves 104 and 106 and minimizes the friction between the head 22 and the ring 12.

Tongue 108 and groove 104 are located a distance d1 from a base surface 112. The tongue 110 and groove 106 are located a distance d2 from the base surface 112. The distance d1 may be greater than the distance d2 to provide a keying function for the assembly of the head 22 to the ring 12. The unequal distances insure that the head 22 is assembled onto the ring 12 so that the third gear 42 is mated with the gear rack 46.

Figure 10A:
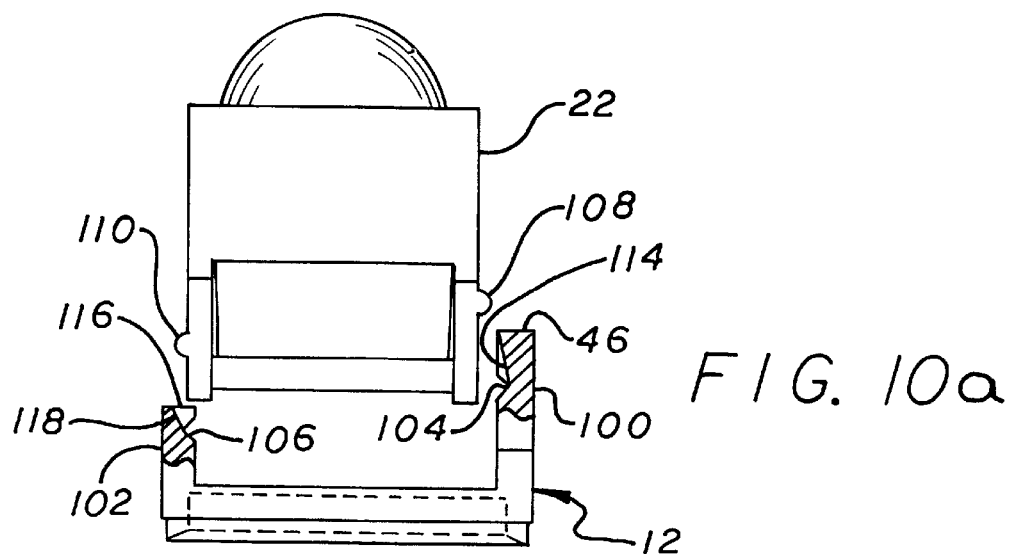
FIGS. 10a–c are side views showing the head being assembled to the ring taken at line 10—10 of FIG. 9.
Figure 10B:
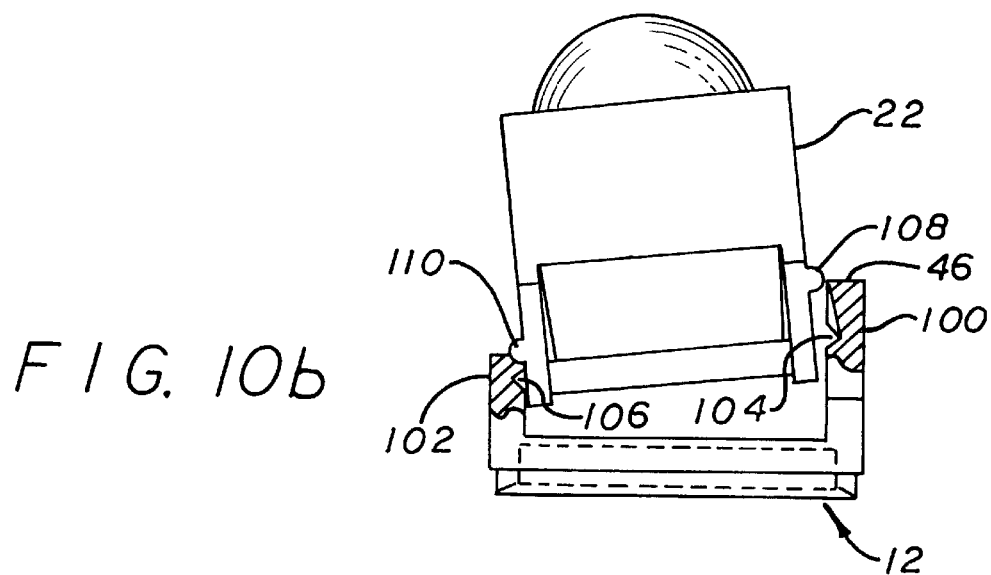
Figure 10C:
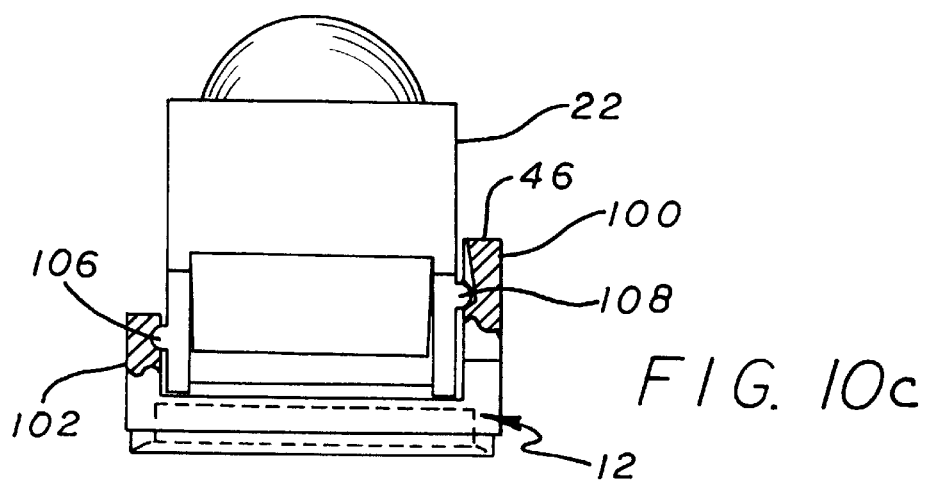

FIGS. 10a–c show a method for assembling the head 22 to the ring 12. The head 22 is moved toward the ring 12 in a vertical direction as indicated by the arrow. A portion of the first sidewall 100 may have a chamfered surface 114 that tapers inwardly from the gear rack 46 to the groove 104 as shown in FIG. 8. Likewise, a portion of the second sidewall 102 may have a chamfered surface 116 that tapers outwardly from a top surface 118 to the groove 106. The inward taper of the chamfered surface 114 leaves sufficient area on the top surface of the first sidewall 100 for the gear rack 46.

A surgeon can push down on the head 22 so that the tongues 108 and 110 slide down the chamfered surfaces 114 and 118. The head 22 may be slightly tilted so that the tongue 108 clears the gear rack 46. The head 22 can be pushed until the tongues 108 and 110 snap into the grooves 104 and 106 to complete the assembly. The linear bearings of the present invention do not require an alignment of the tongues with the grooves and thus reduce the complexity of assembling the device.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

For example, the tongue and groove arrangement shown in FIGS. 8 and 9 may be implemented into a surgical device which has a single motor and a transmission that couples the gears to the single motor. By way of example, the motor and transmission may be the same or similar to the device shown and described in U.S. Pat. No. Re. 35,421 issued to Ruiz et al., which is hereby incorporated by reference.

What is claimed is:

1. A medical device for cutting a cornea, comprising:
   a ring that has a first sidewall and a second sidewall, said first sidewall having a first groove, said second sidewall having a second groove, said first groove is located a first distance from a base surface of said ring and said second groove is located a second distance from said base surface of said ring, wherein the first distance is different from the second distance;
   a head which has a first tongue that can slide along said first grove and a second tongue that can slide along said second groove, said first tongue being located a first distance from a bottom surface of said head and said second tongue being located a second distance from said bottom surface so that said head can be assembled onto said ring in only one orientation;
   said first tongue being located a first distance from a bottom surface of said head and said second tongue being located a second distance from said bottom surface so that said head can only be assembled onto said ring in one orientation;
   a blade that is coupled to said head; and
   a drive assembly that can move said head relative to said ring and said blade relative to said head.

2. The medical device of claim 1, wherein said first sidewall includes a chamfered surface that tapers to said first groove.

3. The medical device of claim 2, wherein said second sidewall includes a chamfered surface that tapers to said second groove.

4. The medical device of claim 1, wherein said second sidewall includes a chamfered surface that tapers to said second groove.

5. The medical device of claim 1, wherein said first wall has a gear rack.

6. The medical device of claim 1, wherein said first and second grooves each have a V-shape and said first and second tongues each have a radial outer surface.

7. The medical device of claim 1, wherein said drive assembly includes a first drive mechanism that moves said head relative to said ring and a second drive mechanism that moves said blade relative to said head.

8. A method for assembling a head to a ring of a surgical device for cutting a cornea, wherein the head houses a blade, comprising:

pushing a part of tongues of a head into a pair of grooves of a ring in a direction that is essentially perpendicular to a longitudinal axis of the one of the grooves.

9. A medical device for cutting a cornea, comprising:

a ring that has a top surface, a first sidewall and a second sidewall, said first sidewall having a first groove, said second sidewall having a second groove, said first sidewall has a chamfered surface that tapers into said first groove;

a head which has a first tongue that can slide along said first groove and a second tongue that can slide along said second groove, said head can be assembled onto said ring from said top surface;

a blade that is coupled to said head; and, a drive assembly that can move said head relative to said ring and said blade relative to said head.

10. The medical device of claim 9, wherein said first wall has a gear rack.

11. The medical device of claim 9, wherein said second sidewall includes a chamfered surface that tapers to said second groove.

12. The medical device of claim 9, wherein said first groove is located a first distance from a base surface of said ring and said second groove is located a second distance from said base surface of said ring, wherein the first distance is different from the second distance.

13. The medical device of claim 9, wherein said first and second grooves each have a V-shape and said first and second tongues each have a radial outer surface.

14. The medical device of claim 9, wherein said drive assembly includes a first drive mechanism that moves said head relative to said ring and a second drive mechanism that moves said blade relative to said head.

* * * * *